(12) United States Patent
Park et al.

(10) Patent No.: US 10,001,467 B2
(45) Date of Patent: Jun. 19, 2018

(54) APPARATUS AND METHOD FOR DETECTING MICROBES OR BACTERIA

(71) Applicant: Korea Advanced Institute of Science and Technology, Daejeon (KR)

(72) Inventors: YongKeun Park, Daejeon (KR); Jonghee Yoon, Daejeon (KR); KyeoReh Lee, Daejeon (KR)

(73) Assignee: Korea Advancad Institute of Science and Technology (KR)

( * ) Notice: Subject to any disclaimer, the term of this patent is extended or adjusted under 35 U.S.C. 154(b) by 37 days.

(21) Appl. No.: 15/170,508

(22) Filed: Jun. 1, 2016

(65) Prior Publication Data

US 2017/0138923 A1 May 18, 2017

(30) Foreign Application Priority Data

Nov. 17, 2015 (KR) .......................... 10-2015-0160915
Mar. 10, 2016 (KR) .......................... 10-2016-0028966

(51) Int. Cl.
*G01N 21/47* (2006.01)
*G01N 33/483* (2006.01)
*G01N 33/02* (2006.01)
*G01N 21/49* (2006.01)

(52) U.S. Cl.
CPC ........... *G01N 33/483* (2013.01); *G01N 21/49* (2013.01); *G01N 33/02* (2013.01); *G01N 2201/066* (2013.01); *G01N 2201/06113* (2013.01)

(58) Field of Classification Search
CPC ..... G01N 2201/06113; G01N 2201/12; G01N 2021/4709; G01N 21/45; G01N 15/1434; G01N 15/1436; G01N 2015/1454; G01N 2201/062; G01N 33/02; G01N 33/487; G01N 2015/1497; G01N 2021/399; G01N 2021/479
See application file for complete search history.

(56) References Cited

U.S. PATENT DOCUMENTS

| 6,076,010 A | 6/2000 | Boas et al. |
| 2004/0070756 A1* | 4/2004 | Rastopov ........... G01N 15/0211 356/338 |
| 2005/0225752 A1* | 10/2005 | Takai ................. G01N 21/4795 356/237.1 |

(Continued)

FOREIGN PATENT DOCUMENTS

KR 20150050265 A 5/2015

OTHER PUBLICATIONS

Vincitorio; "Dynamic Speckle Study of Microbial Growth"; VI International Conference on Speckle Metrology; 2015; vol. 9660.
(Continued)

*Primary Examiner* — Michael P Stafira
(74) *Attorney, Agent, or Firm* — Hayes Soloway PC (57) ABSTRACT

An apparatus and method for detecting microbes use laser speckles. The apparatus includes a light source configured to irradiate light into a sample to detect microbes, and a measuring part configured to measure laser speckles, which are formed due to a multiple scattering of the light which is incident into the sample, every reference time and to measure concentration of the microbes contained in the sample based on temporal correlation of the measured laser speckles.

13 Claims, 7 Drawing Sheets

(56) References Cited

U.S. PATENT DOCUMENTS

| | | | |
|---|---|---|---|
| 2006/0094109 A1* | 5/2006 | Trainer | G01N 15/1456 |
| | | | 435/288.7 |
| 2008/0106737 A1 | 5/2008 | Weichselbaum et al. | |
| 2012/0022381 A1 | 1/2012 | Tearney et al. | |
| 2012/0095354 A1* | 4/2012 | Dunn | A61B 5/0261 |
| | | | 600/504 |
| 2012/0199741 A1* | 8/2012 | Wagner | C12N 5/0612 |
| | | | 250/338.1 |
| 2013/0144137 A1* | 6/2013 | Zalevsky | A61B 5/4504 |
| | | | 600/314 |
| 2015/0276571 A1* | 10/2015 | Hajjarian | G01N 21/41 |
| | | | 73/54.02 |
| 2015/0374246 A1* | 12/2015 | Yelin | A61B 5/0261 |
| | | | 600/479 |

OTHER PUBLICATIONS

Ramirez-Miquet; "*Escherichia coli* Activity Characterization Using a Laser Dynamic Speckle Technique"; Revista Cubana De Fisica; Dec. 2011; vol. 28 No. 1E.

Zheng; "Feature information extraction from dynamic biospeckle"; Applied Optics; Jan. 10, 1994; p. 231-237; vol. 33, No. 2.

\* cited by examiner

180
APPARATUS AND METHOD FOR DETECTING MICROBES OR BACTERIA

CROSS-REFERENCE TO RELATED APPLICATIONS

A claim for priority under 35 U.S.C. § 119 is made to Korean Patent Application No. 10-2015-0160915 filed Nov. 17, 2015, and Korean Patent Application No. 10-2016-0028966 filed Mar. 10, 2016, in the Korean Intellectual Property Office, the entire contents of which are hereby incorporated by reference.

BACKGROUND

Embodiments of the inventive concept described herein relate to technology for detecting or measuring microbes or bacteria through laser speckles from food.

Putrefaction of food is a process of decomposing protein into amine due to multiplication of microbes or bacteria. According to decomposition into amine, food emits a stench and generates a biotoxin. That is, the food is rotten. In the case of ingesting rotten food, an intaker could be poisoned by the rotten food. Therefore, measuring microbes or bacteria from food is very significant for food management and intakers' health.

There are several methods for measuring microbes or bacteria, such as microorganism culture, mass spectrometry, and nuclear magnetic resonance. For the microorganism culture, the mass spectrometry, and the nuclear magnetic resonance are advantageous to microscopic measurement of specific types of microbes or bacteria, but take a long time for preparing samples and require expensive, highly precise, and complicated apparatuses There is besides a technique for measuring microbes or bacteria using an optical manner. For instance, optical measurements include Raman spectrometry and multispectral imaging, but require complicated optical systems, specialized knowledge and laboratory-level facilities operating the complicated optical systems, and a long time for measurement, thus difficult to be employed in food factories or general homes.

Although food is distributed as a matter of course after quality inspection, it is not easily feasible to measure the degree of freshness of food, which is on distribution or in storage, after a shelf life. Moreover, as microbes or bacteria easily multiply even under low temperature (e.g., 4° C.) as well as under room temperature, it is necessary for general persons to easily measure microbes or bacteria from food, which is even in storage, in homes or markets.

Korean Patent Publication No. 10-2015-0050265 discloses the technique of irradiating ultraviolet rays into microbes and receiving a fluorescent spectrum of amino acid constituting protein of the microbes.

SUMMARY

Embodiments of the inventive concept provide an apparatus and method for detecting microbes or bacteria from food, which is in storage, through laser speckles.

Additionally, embodiments of the inventive concept provide an apparatus and method for constructing an optical system with a light source and a camera, and detecting quickly and precisely presence or absence and activity of microbes or bacteria from food even without specialized knowledge for operating the optical system.

In accordance with an aspect of the inventive concept, an apparatus for detecting microbes may include a light source configured to irradiate light into a sample to detect microbes, and a measuring part configured to measure laser speckles, which are formed due to a multiple scattering of the light which is incident into the sample, every reference time and to measure concentration of the microbes, which are contained in the sample, based on temporal correlation of the measured laser speckles.

In an embodiment, the measuring part may be configured to measure the concentration of the microbes by analyzing a variation of a pattern of the later speckles that are measured every the reference time.

In another embodiment, the measuring part may be configured to measure a distribution of the microbes, which are contained in the sample, based on a standard deviation of light intensity of the laser speckles.

In still another embodiment, the measuring part may be configured to calculate a standard deviation of light intensity based on constructive interference and destructive interference that vary with activity of microbes or bacteria contained in the sample.

In still another embodiment, the light source and the measuring part may be restrictive in motion until the light is irradiated into the sample and the concentration of the microbes is measured.

In still another embodiment, the light source and the measuring part may be configured to construct a reflective optical system.

In still another embodiment, the light source and the measuring part may be configured to construct a transmittal optical system.

In still another embodiment, the light source and the measuring part may be configured in a package type.

In accordance with another aspect of the inventive concept, a method for detecting microbes may include irradiating light into a sample to detect microbes, measuring laser speckles, which are formed due to a multiple scattering of the light incident on the sample, every reference time, and measuring concentration of microbes, which are contained in the sample, based on temporal correlation of the measured laser speckles.

In an embodiment, the measuring of the concentration of the microbes may include measuring the concentration of the microbes by analyzing a variation of the laser speckles measured every the reference time.

In another embodiment, the measuring of the concentration of the microbes may include measuring a distribution of bacteria, which are contained in the sample, based on a standard deviation of light intensity of the laser speckles.

In still another embodiment, the measuring of the concentration of the microbes may include measuring a standard deviation of light intensity based on constructive interference and destructive interference that vary with activity of microbes or bacteria contained in the sample.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereafter, embodiments of the inventive concept will be described in conjunction with the accompanied figures.

These embodiments are associated with technology for measuring concentration and activity of microbes or bacteria, which are contained in food, using temporal correlation of laser speckles. Especially, these embodiments are associated with technology for quickly and accurately measuring concentration of microbes or bacteria by constructing an optical system simply with a light source, which irradiates light into food, and with a camera which detects microbes from the food.

Laser speckles are generated by interference of light. For example, laser speckles may mean grain-shaped patterns (or figures) which are hardly focused with high contrast generated from the surface of a sample when a laser is irradiated into a sample such as food and drink.

In these embodiments, an optical system formed of a light source and a camera may be constructed in various types and may be installed in food storage such as refrigerator, freezer, or kimchi refrigerator, or may be prepared even in a production or distribution line for food. Additionally, such an optical system may be even formed in a portable package type which allows a user to carry it by hand.

Figure 1:
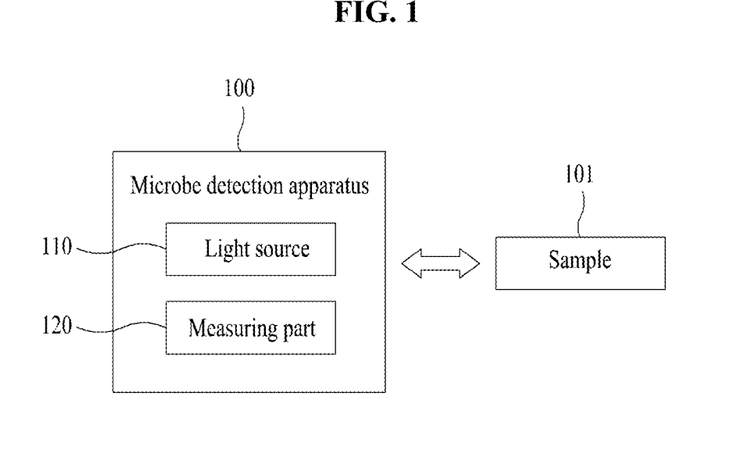
FIG. 1 is a block diagram illustrating an internal configuration of an apparatus for detecting microbes in an embodiment of the inventive concept.
Figure 2:
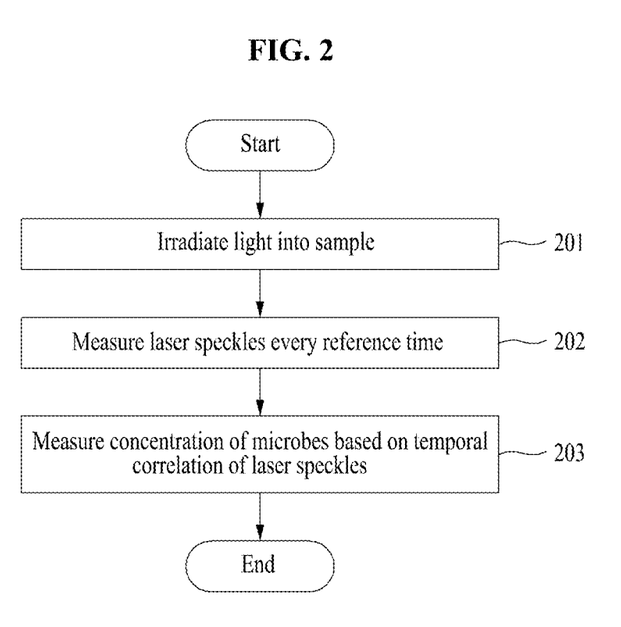
FIG. 2 is a flow chart showing a method for detecting microbes from a sample through laser spackles in an embodiment of the inventive concept.

FIG. 1 is a block diagram illustrating an internal configuration of an apparatus for detecting microbes in an embodiment of the inventive concept, and FIG. 2 is a flow chart showing a method for detecting microbes from a sample through laser spackles in an embodiment of the inventive concept.

Referring to FIG. 1, a microbe detection apparatus 100 may include a light source 110 and a measuring part 120. The steps 201 to 203 of FIG. 2 may be performed by the elements, for example, the light source and the measuring part, of the microbe detection apparatus shown in FIG. 1.

In the step 201, the light source 110 may irradiate light into a sample 101 to detect microbes from the sample 101.

For example, a laser may be used for the light source 110. The light source 110 may irradiate a laser into the sample 101 such as meat or seafood. The sample 101, as food containing microbes or bacteria, may be prepared through various ways. For example, the sample may be used even with the whole body or a mince of food. Otherwise, the sample may be also prepared by biopsy with an injector. Otherwise, the sample may be prepared even with a device such as membrane to which microbes or bacteria easily migrate.

In step 202, the measuring part 120 may measure laser speckles, which are generated by a multiple scattering of light incident on the sample 101, every reference time.

In step 203, the measuring part 120 may measure concentration of microbes or bacteria based on temporal correlation of the measured laser speckles.

For example, the measuring part 120 may be used with a camera which is a device for photographing an image. If a laser is irradiated into the sample 101, the incident light may generate laser speckles through a multiple scattering. Laser speckles are generated by interference of light. Therefore, if there is no activity in the sample, an interference pattern may be uniform along time. In the case that microbes or bacteria are present in the sample, laser speckles may vary with activity of microbes or bacteria along time. Accordingly, whether microbes or bacteria are present in the sample may be quickly determined based on a pattern of laser speckles which vary along time.

As an example, the measuring part 120 as a camera may photograph laser speckles, which are formed on the surface of the sample 101, to generate an image of the laser speckles. During this, the measuring part 120 may measure laser speckles by photographing the laser speckles every reference time. Then, the measuring part 120 may calculate temporal correlation coefficients between images through laser speckle images which are generated every reference time, and may determine whether microbes or bacteria are present in the sample 101 based on the temporal correlation coefficients. And the measuring part 120 may measure concentration of microbes or bacteria based on a variation of the temporal correlation coefficients.

While measuring laser speckles generated in the sample 101, the optical system formed of the light source 110 and the measuring part 120 may be restrictive in motion. For example, concentration of microbes or bacteria may be accurately measured under the condition without motion of the light source 110 and the measuring part 120 until the concentration of microbes or bacteria is completely measured after irradiation of light into the sample 101. The optical system may be constructed in a reflective, transmittal, or package type. Diverse ways of constructing the optical system will be described below in conjunction with FIGS. 3 to 5.

Figure 3:
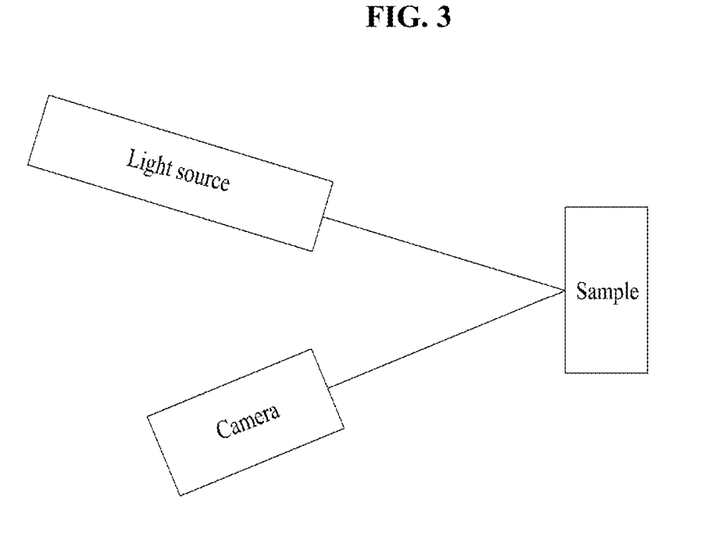
FIG. 3 illustrates a case of constructing an optical system in a reflective type according to an embodiment of the inventive concept.

FIG. 3 illustrates a case of constructing an optical system in a reflective type according to an embodiment of the inventive concept.

Referring to FIG. 3, a laser incident on a sample may reflectively exit with a part of light due to a multiple scattering because of optical non-uniformity of the sample. Then, a camera may measure laser speckles by taking a laser speckle signal which is generated through reflective exit of light from the sample due to the optical non-uniformity of the sample.

In FIG. 3, the light source may not be limited to its wavelength and intensity of light. A type of the camera may be preferred with one capable of measuring second-dimensional information, but may be used even with one capable of measuring one-dimensional information.

As also In FIG. 3, there is no specification for positions of the light source and the sample. The camera measuring a reflected laser speckle signal may be positioned to render one measured speckle size to correspond with a size equal to or larger than two or three pixels. For example, the camera may be slantingly placed with an angle θ, facing the plane on which light is incident, to measure a laser spackle signal which is generated by reflection of light from the sample.

Figure 4:
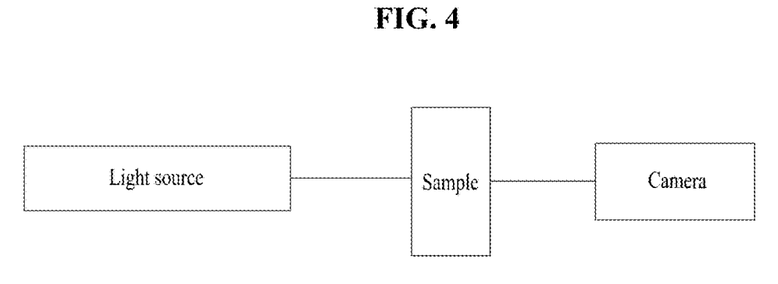
FIG. 4 illustrates a case of constructing an optical system in a transmittal type according to an embodiment of the inventive concept.

FIG. 4 illustrates a case of constructing an optical system in a transmittal type according to an embodiment of the inventive concept.

Referring to FIG. 4, a laser incident on a sample may transmit and exit with a part of light through a multiple scattering due to optical non-uniformity of the sample. Then, a camera may measure laser speckles, which are caused from light transmission through the sample, by photographing a laser speckle signal which is generated by transmission and exit of light through the sample.

In FIG. 4, the light source may not be limited to its wavelength and intensity of light. A type of the camera may be preferred with one capable of measuring second-dimensional information, but may be used even with one capable of measuring one-dimensional information.

As also In FIG. 4, there is no specification for positions of the light source and the sample. The camera measuring a transmitted laser speckle signal may be positioned to render one measured speckle size to correspond with a size equal to or larger than two or three pixels.

Figure 5:
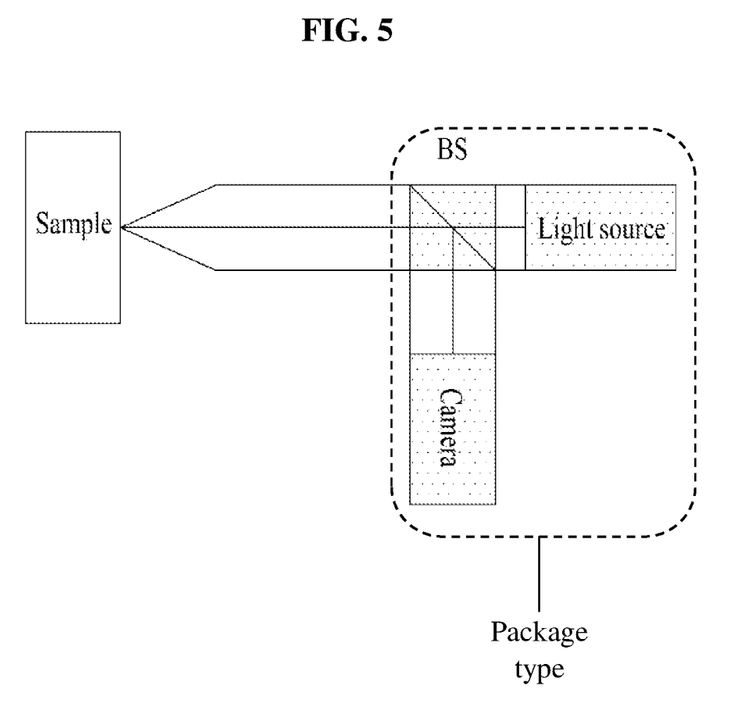
FIG. 5 illustrates a case of constructing an optical system in a package type according to an embodiment of the inventive concept.

FIG. 5 illustrates a case of constructing an optical system in a package type according to an embodiment of the inventive concept.

With respect to FIG. 5, a laser incident on a sample may cause a multiple scattering due to the optical non-uniformity to make a part of light reflectively exit. The reflected light may be changed in path through a beam splitter BS and then a camera may measure laser speckles which are induced in the sample. For example, the beam splitter BS may be placed between a light source and a sample and may change a path of light reflectively exiting from the sample. The camera may measure laser speckles which are generated by reflection and path change of light through the sample.

In FIG. 5, the light source may not be limited to its wavelength and intensity of light. A type of the camera may be preferred with one capable of measuring second-dimensional information, but may be used even with one capable of measuring one-dimensional information.

Additionally, In FIG. 5, the light source, the beam splitter BS, and the camera may be fixed in a package type acting as a single module, and may be positioned to render a size of one speckle, which is measured by the camera, to correspond with a size equal to or larger than two or three pixels.

Referring to FIG. 5, in the case of constructing an optical system in a package type, i.e., a portable type, there is a need of caution to prevent an optical system from moving while measuring laser speckles which are generated in a sample.

Figure 6:
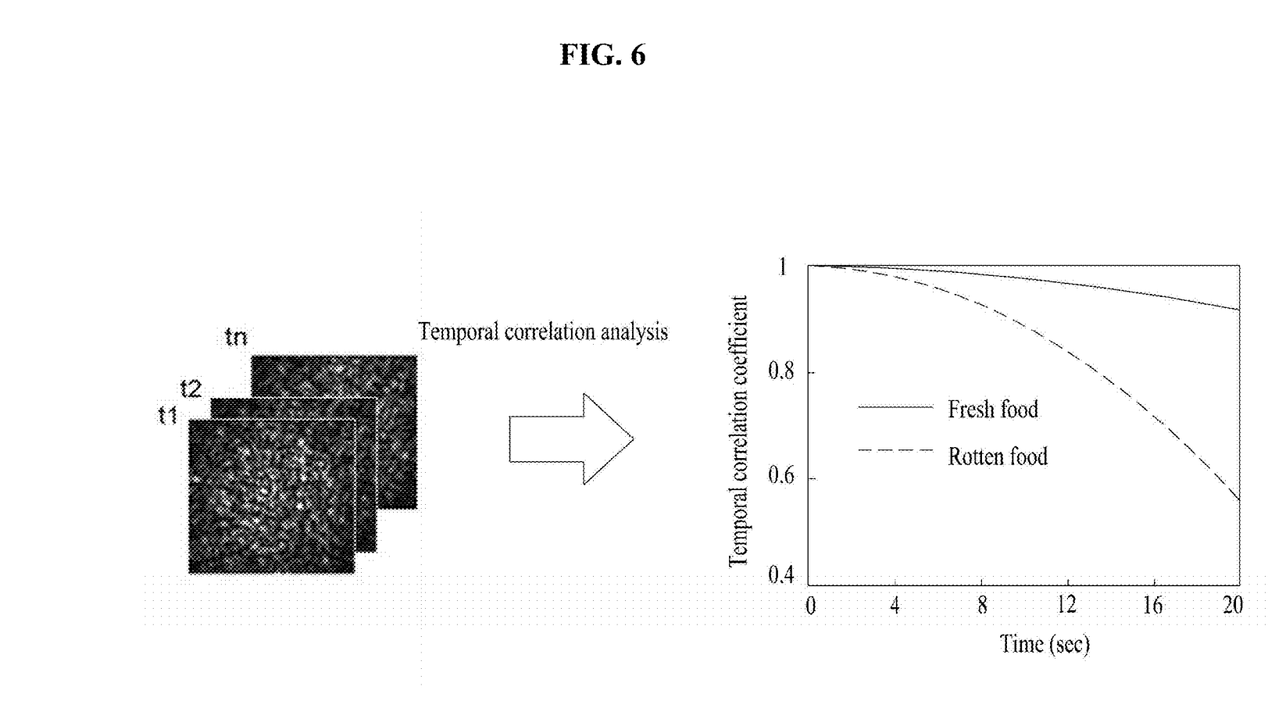
FIG. 6 illustrates a method for measuring concentration of microbes or bacteria by analyzing temporal correlation of laser speckles in an embodiment of the inventive concept.

FIG. 6 illustrates a method for measuring concentration of microbes or bacteria by analyzing temporal correlation of laser speckles in an embodiment of the inventive concept.

With respect to FIG. 6, measuring concentration of microbes or bacteria through analysis with temporal correlation of laser speckles may be performed by the measuring part 120 of FIG. 1.

Referring to FIG. 6, a light source 110 may irradiate a laser into a sample 101 every reference time and the measuring part 120 may measure laser speckles which are generated due to a multiple scattering. During this, the measuring part 120 may analyze laser speckle images which are generated every reference time and may measure concentration of microbes or bacteria from the sample 101 through a variation of temporal correlation coefficients.

Temporal correlation of the measured laser speckles may be calculated by Equation 1 as follows.

$$\bar{C}(x, y; \tau) = \frac{1}{T - \tau} \sum_{t=1}^{T-\tau} \bar{I}(x, y; t) \bar{I}(x, y; t + \tau) \delta t \quad \text{[Equation 1]}$$

In Equation 1, C may denote a temporal correlation coefficient, $\bar{I}$ may denote standardized light intensity, (x,y) may denote a pixel coordinate of a camera, t may denote a measuring time, T may denote the total measuring time, and may denote a time lag.

From Equation 1, temporal correlation coefficients may be calculated. Concentration of microbes or bacteria may be measured through an analysis for a time when the temporal correlation coefficient is equal to or lower than a specific value. Higher concentration of microbes or bacteria may shorten so much a time when the temporal correlation coefficient is equal to or lower than the specific value. A reference for the specific value may be variable depending on types of food and microbes.

As an example, the measuring part 120 may determine from laser speckle images whether microbes or bacteria are present in the sample 101 by finding whether laser speckles are changed in pattern along time. For example, if there is no activity in the sample, laser speckles appear with a uniform interference pattern along time. That is, if there is no activity of microbes or bacteria in the sample, a uniform interference pattern of laser speckles are found from laser speckle images taken every reference time. As such, in the case that laser speckle images show a uniform interference pattern, the measuring part 120 may determine that microbes or bacteria are absent in the sample 101.

On the other hand, in the case that a laser speckle pattern varies without an interference pattern, the measuring part 120 may determine that microbes or bacteria are present in the sample 101. That is, in the case that microbes or bacteria are present in the sample 101 which is food, it may be determined as multiplication and continuous activity of the microbes or bacteria along time. This activity of microbes or bacteria may cause a continuous change of laser speckle pattern along time. According as that, from laser speckle images measured every reference time, the measuring part 120 may determine that microbes or bacteria are present in the sample 101 in the case that a laser speckles pattern are changed in a degree equal to or larger than a specific error range.

During this, a variation degree of laser speckles may be determined in accordance with concentration of microbes or bacteria. The concentration of microbes or bacteria may be measured through a temporal correlation analysis. For example, a standard deviation of light intensity of laser speckles may be used for measuring a variation degree of the laser speckles.

Figure 7:
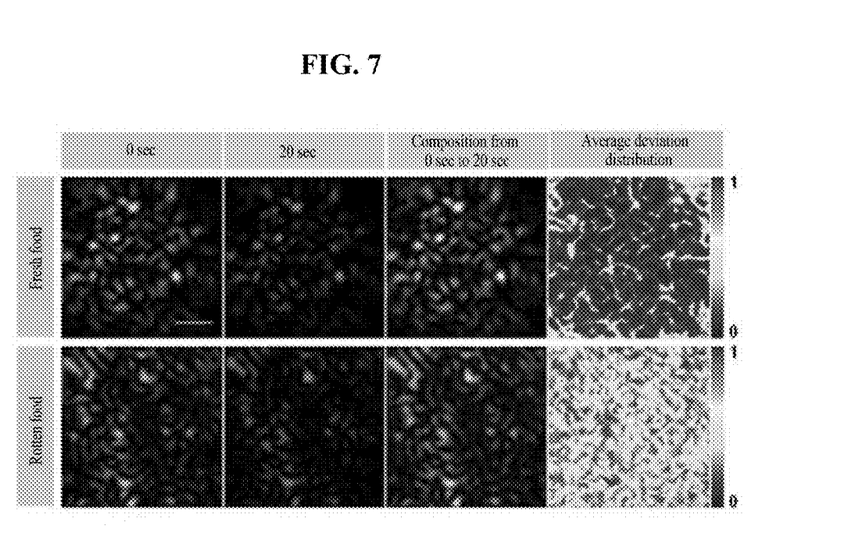
FIG. 7 illustrates a standard deviation of light intensity of laser speckles measured along time in an embodiment of the inventive concept.

FIG. 7 illustrates a standard deviation of light intensity of laser speckles measured along time in an embodiment of the inventive concept.

Referring to FIG. 7, the measuring part 120 may calculate a standard deviation of light intensity of laser speckles from laser speckle images measured every reference time.

According to continuous activity of microbes or bacteria in the sample 101, constructive interference and destructive interference may vary in correspondence with the activity. Due to variation of the constructive interference and the destructive interference, the light intensity may be variable in a large degree. Then, the measuring part 120 may obtain a standard deviation, which represents a variation degree of the light intensity, to find positions of microbes or bacteria in the sample 101, and then may measure a distribution of the microbes or bacteria.

For example, the measuring part 120 may compose laser speckle images taken every specific time interval, and may calculate a standard deviation of light intensity of laser speckles along time from the composed image. A standard deviation of light intensity of laser speckles along time may be calculated by Equation 2 as follows.

$$S(x, y) = \sqrt{\frac{1}{T}\sum_{t=1}^{T}(I_t(x, y) - \bar{I})^2} \quad \text{[Equation 2]}$$

In Equation 2, S may denote a standard deviation, (x,y) may denote a camera pixel coordinate, T may denote the total measuring time, t may denote a measuring time, $I_t$ may denote light intensity measured at time t, and $\bar{I}$ may denote standardized light intensity.

Depending on activity of microbes or bacteria, constructive interference and destructive interference are changed in pattern and a standard deviation calculated by Equation 2 becomes larger. Based thereon, it may be permissible to measure concentration of microbes or bacteria of the sample.

Additionally, the measuring part 120 may measure a distribution, i.e., concentration, of microbes or bacteria based on linear relativity between a standard deviation of light intensity of laser speckles and concentration of the microbes or bacteria.

According to embodiments of the inventive concept, it may be allowable to detect microbes or bacteria from food, which is in storage, through laser speckles.

Additionally, it may be allowable for embodiments of the inventive concept to detect easily and simply microbes from food through an optical system, with a light source and a camera.

While embodiments of the present disclosure have been shown and described with reference to the accompanying drawings thereof, it will be understood by those skilled in the art that various changes and modifications in form and details may be made therein without departing from the spirit and scope of the present disclosure as defined by the appended claims and their equivalents. For example, it may be allowable to achieve desired results although the embodiments of the present disclosure are preformed in other sequences different from the descriptions, and/or the elements, such as system, structure, device, circuit, and so on, are combined or assembled in other ways different from the descriptions, replaced or substituted with other elements or their equivalents.

Therefore, other implementations, other embodiments, and equivalents of the appended claims may be included in the scope of the appended claims.

What is claimed is:

1. An apparatus for detecting microbes, the apparatus comprising:
    a light source configured to irradiate light into a sample to detect microbes; and
    a measuring part configured to measure laser speckles, which are formed due to a multiple scattering of the light which is incident into the sample, every reference time and to measure concentration of the microbes, which are contained in the sample, based on temporal correlation of the measured laser speckles, wherein the measuring part is configured to measure laser speckles based on constructive interference and destructive interference that vary with activity of microbes contained in the sample, and
    wherein the measuring part is configured to calculate a temporal correlation coefficient based on temporal correlation of the measured laser speckles and measure concentration of the microbes, which are contained in the sample, using an analysis for a time when the temporal correlation coefficient is equal to or lower than a specific value.

2. The apparatus of claim 1, wherein the measuring part is configured to measure the concentration of the microbes by analyzing a variation of a pattern of the laser speckles that are measured every reference time.

3. The apparatus of claim 1, wherein the measuring part is configured to measure a distribution of the microbes, which are contained in the sample, based on a standard deviation of light intensity of the laser speckles.

4. The apparatus of claim 1, wherein the measuring part is configured to calculate a standard deviation of light intensity based on the constructive interference and the destructive interference.

5. The apparatus of claim 1, wherein the light source and the measuring part are restrictive in motion until the light is irradiated into the sample and the concentration of the microbes is measured.

6. The apparatus of claim 1, wherein the light source and the measuring part are configured to construct a reflective optical system.

7. The apparatus of claim 1, wherein the light source and the measuring part are configured to construct a transmittal optical system.

8. The apparatus of claim 1, wherein the light source and the measuring part are configured in a package type.

9. The apparatus of claim 1, further comprising:
    a beam splitter configured to change a path of light that is incident on the sample and reflectively exits from the sample through a multiple scattering.

10. A method for detecting microbes, the method comprising:
    irradiating light into a sample to detect microbes;
    measuring laser speckles, which are formed due to a multiple scattering of the light incident on the sample, every reference time, wherein the laser speckles are measured based on constructive interference and destructive interference that vary with activity of microbes contained in the sample; and
    measuring concentration of microbes, which are contained in the sample, based on temporal correlation of the measured laser speckles,
    wherein the measuring concentration of microbes comprises measuring laser speckles based on constructive interference and destructive interference that vary with activity of microbes contained in the sample, and
    wherein the measuring concentration of microbes comprises calculating a temporal correlation coefficient based on temporal correlation of the measured laser speckles and measuring concentration of the microbes, which are contained in the sample, using an analysis for a time when a temporal correlation coefficient is equal to or lower than a specific value.

11. The method of claim 10, wherein the measuring of the concentration of the microbes comprises:
    measuring the concentration of the microbes by analyzing a variation of the laser speckles measured every reference time.

12. The method of claim 10, wherein the measuring of the concentration of the microbes comprises:
 measuring a distribution of bacteria, which are contained in the sample, based on a standard deviation of light intensity of the laser speckles.

13. The method of claim 10, wherein the measuring of the concentration of the microbes comprises:
 measuring a standard deviation of light intensity based on the constructive interference and the destructive interference.

* * * * *